United States Patent [19]

Varani

[11] 4,208,279
[45] Jun. 17, 1980

[54] METHOD AND APPARATUS FOR PROCESSING ANIMAL WASTE

[75] Inventor: Frederick T. Varani, Boulder, Colo.

[73] Assignee: Bio-Gas of Colorado, Inc., Arvada, Colo.

[21] Appl. No.: 36,580

[22] Filed: May 7, 1979

[51] Int. Cl.² ............................................. C02C 1/16
[52] U.S. Cl. .................................... 210/12; 210/164; 210/180; 119/16; 119/28; 48/197 A
[58] Field of Search ................ 119/16, 27, 28; 210/2, 210/12, 16, 71, 154, 153, 163, 164, 165, 175, 180; 48/197 A

[56] References Cited

U.S. PATENT DOCUMENTS

| 2,892,545 | 6/1959 | Griffith | 210/16 |
|---|---|---|---|
| 3,010,581 | 11/1961 | Knapp et al. | 210/16 |
| 3,418,975 | 12/1968 | Smith | 119/28 |
| 3,601,096 | 8/1971 | Rutherford | 119/16 |
| 3,927,644 | 12/1975 | Nafziger | 210/167 |
| 3,933,628 | 1/1976 | Varani | 210/12 |
| 4,008,689 | 2/1977 | Albers | 119/28 |

*Primary Examiner*—Ernest G. Therkorn
*Attorney, Agent, or Firm*—Edwin L. Spangler, Jr.

[57] ABSTRACT

This invention relates to an improved apparatus for both processing and removing animal waste products from a pit continually supplied therewith which comprises a ramp-like lid partially covering the pit and cooperating with the contents thereof to seal the latter from the atmosphere except where the waste products enter, a spray at the head of the ramp for flushing the waste materials down and off the lower end thereof into the pit, a heater buried in the material within the pit effective to maintain the temperature thereof at a level conducive to facilitate anaerobic digestion of the bio-degradable portion thereof, means for piping off the bio-gas generated underneath the lid and using a portion thereof to fire the heater, and means for draining the pit remote from the point where the fresh waste enters same, such means being adapted to maintain a near constant level of material within the pit effective to preserve the seal and discharge material therefrom without admitting air thereto. The invention also encompasses the improved method for emptying such pits which includes partially covering them with a ramp which cooperates with the material housed therein to seal off the latter from the atmosphere except where it enters, flushing the waste material deposited on the ramp off the lower end thereof into the pit, heating the contents of the pit to a temperature selected to promote anaerobic digestion of the bio-degradable portion thereof, seeding the pit with bacterial capable of breaking the bio-degradable portion down and generate a bio-gas therefrom at the selected temperature, using at least a part of the energy contained in the bio-gas thus produced to heat the digesting mass, and using the fresh waste material entering the pit to push the digested material therefrom.

8 Claims, 3 Drawing Figures

METHOD AND APPARATUS FOR PROCESSING ANIMAL WASTE

Over much of the midwestern United States and elsewhere, much of the livestock, particularly cattle and hogs, are raised indoors rather than on the open range. These areas are generally those in which excellent feed grain crops like corn are raised but, instead of being marketed as such, they are fed to the farmer's own livestock which in turn are sold for market beef, pork and the like.

The buildings in which these animals are confined, while structurally somewhat minimal, nevertheless cost at current prices somewhere around $250.00 per animal. Thus, a thousand cow unit involves an expenditure of a quarter of a million dollars which is certainly a significant capital outlay. In addition, there are other expenses of a substantial nature, a few of which will be mentioned presently. These buildings vary in size depending upon the number and type of animals that will be housed therein.

A typical cattle confinement building will be divided up into a series of pens arranged in a long row with each pen holding maybe 50 cows. The row of pens will oftentimes be raised up above the surrounding ground and provided with service roadways alongside it where trucks can introduce feed into common feed troughs running the length thereof. Lagoons for waste materials generally lie adjacent these buildings.

Shed roofs cover the pens and some have walls while others do not but regardless, they are seldom if ever heated which leaves them subject to both the elements and extreme temperatures. Underneath each pen is a large concrete-lined waste basin covered by an open grid upon which the animals walk. This grid or coarse grill functions as both the floor of the pen and a screen effective to pass the excrement into the pit or basin therebeneath as the animals move around. Access openings in the floor are used to pump the waste materials from the basin and into the lagoon alongside.

A fifty cow pen will be somewhere around 50 feet long, 20 feet wide and 8 feet or so deep. The build up of solid waste is such that each one must be pumped out at least twice a year and occasionally more often. Under the best of circumstances this is anything but a pleasant job. To begin with, large and expensive equipment is required. A pump costing upwards of $10,000.00 is needed to handle the solid wastes and close to a day's labor is required to empty each pit. The tractor to drive such a pump is large and very expensive, one rated at 150 horsepower being about average.

The customary process is one of first stirring up the waste material until it is of a fairly uniform consistency capable of being pumped. Once the mixture is in a form in which it can be handled, then and only then is it pumped out of the basin. Unfortunately, if this waste material freezes, and it often does in the midwestern United States where many operations of this type are found, the pits cannot be unloaded and if they are full, the pen must be shut down.

Even worse problems exist in hot weather. First of all the odor is nearly intolerable. If the temperature of the waste material gets to a point where it begins to bio-degrade, and it often does, hydrogen sulfide gas is given off which is not only unpleasant but most significant is the fact that it causes stress in the cattle themselves and they do not gain weight as they should. Thus far, efforts at controlling this odor problem have amounted to little more than opening up the roof, perhaps removing the walls or providing some forced ventilation with fans. Once the solid waste is in the settling pond or lagoon, it continues to contaminate the atmosphere with unpleasant odors and little, if anything, of a practical nature can be done about it.

Not infrequently, other solid waste materials find their way into the pits including such things as calves tails and other oddities. The significance of this is that, while the pump can handle manure if it is of the right consistency, other things foul the impeller and generally make the pit-emptying process a more distasteful one that it would be under the best of circumstances.

Bio-degradation of the manure to produce bio-gas for use as a fuel is, of course, a way of converting the waste materials from such an operation into a useful commodity. Unfortunately, however, it does not solve the odor problem or make cleaning the pits one bit easier. Nevertheless, it has now been found in accordance with the teaching of the instant invention that the manure can, in fact, be digested under anaerobic conditions to produce bio-gas while, at the same time, eliminating the pit cleaning operation altogether, significantly reducing the odor problem and reducing the solid waste by about 50%. In the process, the manure is treated in such a manner that it not only becomes easier to handle, it will flow by itself into the catch basin or lagoon. The sludge left over following digestion of the manure is far less objectionable from an odor standpoint and, in addition, shows promise as a feed supplement rich in protein values. The bio-gas, of course, can be used directly as a fuel or subjected to further processing by methods well known in the art.

By eliminating the pumping operation, the pump along with the prime mover to drive it can be eliminated as well as the considerable saving in labor. These cost savings go a long way toward offsetting the cost of the additional equipment necessary in the pits.

All these advantages are realized by the simple, yet unobvious, expedient of providing each pit with a roof-like lid underneath the grating that serves the primary purpose in combination with the waste material contained therein of defining an anaerobic digester. The lid is so designed that it will seal off most of the contents of the pit from the atmosphere thus reducing the odors emanating therefrom and the associated trauma in the animals housed in the pen. The solids confined underneath the roofed-over portion are capable of being bio-degraded under essentially anaerobic conditions; yet, the pit remains open at one end to continually receive additional waste materials deposited therein. Last, but by no means least, is the further function of the lid to serve as a ramp effective to direct the solid wastes deposited thereon down into the pit through the open end thereof.

Water is added to the waste as it enters the pit so that it contains the proper proportion of solids for the best digestion and also to wet it to the point where it will slide easily down the ramp. Heaters within the pit itself maintain the temperature of the waste materials within the range which is ideally suited to maximize the bacterial action and promote the digestion process. These same heaters, of course, prevent the sludge in the pit from freezing and becoming difficult if not impossible to handle. Also, the source of heat to heat the heaters is readily available in the form of the bio-gas generated by the process. Plenty of fuel is generated since as a rough figure, each cow can be expected to produce enough manure to generate from a minimum of 20 up to around 40 cubic feet of bio-gas a day. Bio-gas is a combustible mixture of methane, carbon dioxide and hydrogen sulfide but, even with its impurities having no fuel value, probably less than a third of the gas generated would be needed to operate the heaters even under extreme conditions.

An outlet at the base of the pit remote from the point at which the fresh manure enters is employed to deliver the digested slurry to an overflow box from whence it flows into the lagoon. The degasified slurry consists of only about half the solids that entered the system. At the same time, the slurry is far more dilute and will flow easily out of the pit and into the lagoon.

In addition to the bio-gas, the digested slurry properly processed to remove the bacterial cells is worth around $50/ton as a feed supplement. As a source of organic material to be plowed back into the soil, it is superior to the manure. Regardless of whether the degasified sludge is recycled or otherwise reclaimed, its bulk is reduced by about half and it is far less objectionable from an odor standpoint than the manure. By lessening the odor problem, even the cattle benefit in that they are subject to less stress and, therefore, utilize their feed more efficiently, all of which brings the farmer more money in the marketplace.

It is, therefore, the principal object of the present invention to provide a novel and improved confinement building for animals.

A second objective is the provision of a facility of the type aforementioned wherein the excrement pit beneath the slatted floor is converted to an "in situ" anaerobic digester.

Another object is to provide an improved method for disposing of animal waste generated within a confinement pen.

Still another objective is the provision of a subfloor anaerobic digester that is self-emptying and not only requires no input of energy to sustain its operation but produces an excess of energy.

An additional object is to provide a method and apparatus for producing not one, but two, useful byproducts from manure while, at the same time, eliminating most of the problems associated with its disposal along with the stress produced in the animals due to the odor.

Further objects are to provide an improved facility within which to fatten animals for market which is simple, inexpensive in terms of converting existing facilities, versatile, productive, efficient and virtually labor-free insofar as emptying same is concerned.

Other objects will be in part apparent and in part pointed out specifically hereinafter in connection with the description of the drawings that follows, and in which.

Figure 1:
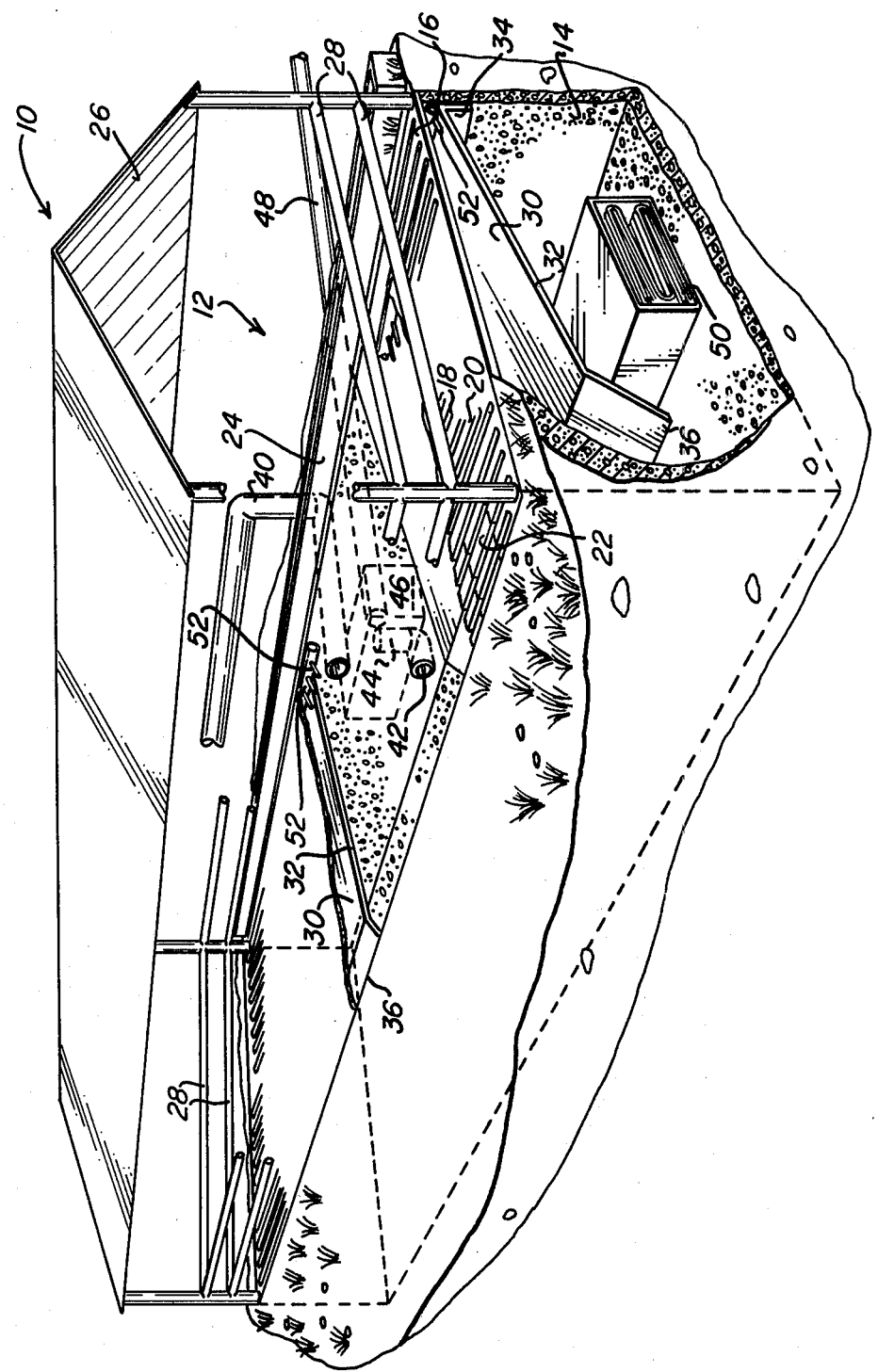
FIG. 1 is a perspective view showing the improved apparatus for processing animal wastes with various and sundry portions thereof having been broken away and sometimes shown in section to better reveal the interior construction.
Figure 2:
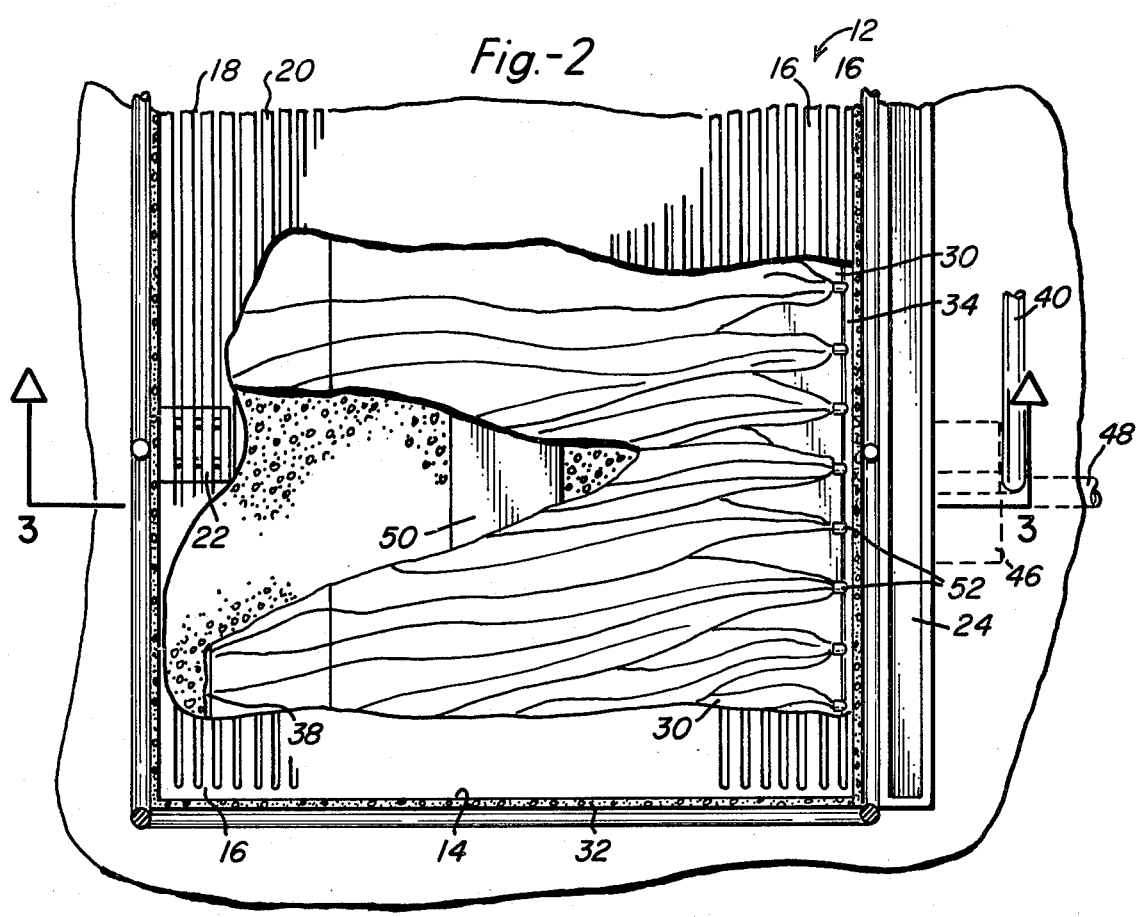
FIG. 2 is a top plan view to a greatly enlarged scale showing one of the pens within the confinement building housing the improved waste treatment apparatus of the instant invention, the roof having been removed as well as sections of the floor, ramp and other features necessary to reveal the interior construction; and, FIG. 3 is a vertical section taken along line 3—3 of FIG. 2.
Figure 3:
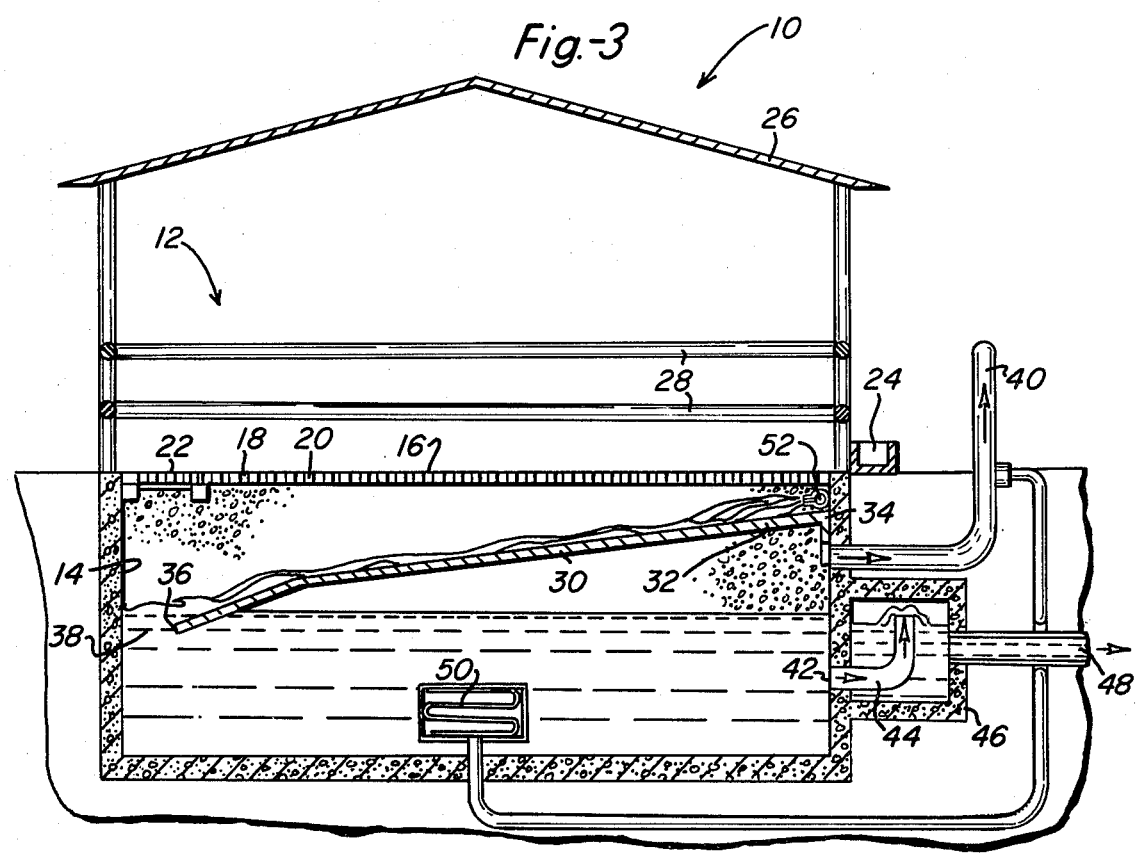

Referring next to the drawings for a detailed description of the present invention, reference numeral 10 has been chosen to broadly designate the confinement building in its entirety and numeral 12 to similarly designate one of the several animal pens customarily contained therein. Basic to the design of such buildings and pens are the concrete-lined pit 14 covered by the slatted floor 16 covering the latter. Excrement deposited on the floor by the animals eventually works its way through the slits 18 between the slats 20 in the floor and down into the pit. As illustrated, a clean out door 22 is provided at one end of the pen.

Other commonplace features of such buildings are trough-like feed bunkers 24 extending along one side of the building, generally in a position to be filled from a truck driving alongside thereof. A shed roof 26 customarily covers the pens and fence-forming barriers of some type 28 confine the animals to their particular pen. Walls may or may not be used and none has been shown.

The improved confinement building of the present invention adds a few simple, yet extremely important, features to the conventional structure just described. They are, first of all, a ramp-like sloping lid 30 located beneath the floor partially covering the pit. The sides 32 as well as one end 34 of this lid are attached to the adjacent walls of the pit so as to maintain an essentially gas-tight seal therewith while the free edge 36 thereof opposite end 34 is immersed in the contents and, at the same time, spaced from the adjacent pit wall so as to leave a gap 38 therebetween. As will be explained presently, the level of material contained in the pit remains essentially constant so that the lid coacts therewith and with three of the four pit walls to prevent air from reaching all but a very small fraction of the contents, namely, that which is exposed within gap 38. Bacteria contained in the pit function in the well-known manner to break down the contents under anaerobic condition to produce a bio-gas consisting of primarily a mixture of methane, carbon dioxide and hydrogen sulfide along with a wet sludge rich in protein and other nutrients. The bio-gas generated in the pit is trapped underneath the lid and constantly drawn off through a suitable gas line 40 connected therein above the level of the digesting mass. As the digestion process proceeds, about half the digesting mass is converted to bio-gas while the remainder is piped off as sludge through outlet 42 near the bottom of the pit. This outlet connects into a standpipe 44 which opens into an overflow box 46. The height of the standpipe governs the level of the contents in the pit thus insuring that it covers the free edge 36 of the lid. The sludge overflowing standpipe 44 drops into the bottom of box 46 where it is drained off to a storage area (not shown) through a drain 48 at the base thereof.

A heater 50 preferably gas-fired, is located in the pit buried in the contents thereof. This heater and others like it in adjoining pens maintains the temperature of the digesting mass at that level which optimizes bacterial action. These temperatures and other features of the anaerobic digestion process are well known in the art and, as such, form no part of the present invention. It should be pointed out, however, that in large scale operations, say a thousand cattle or so, the volume of bio-gas generated far exceeds the normal needs of the average farm where such a facility is located even considering that about a third of the bio-gas generated is recycled to fire the heaters. Part of the remaining gas which, can be burned "as is" so to speak can, of course, be used for other applications around the farm but, generally speaking, there will still be a lot left over. Under some circumstances, scrubbing or otherwise processing the gas that is left may be justified.

Now, as previously noted, lid 30 slopes down toward its free edge 36 thus producing a ramp along which the excrement dropping through the slatted floor slides preparatory to entering the pit through gap 38. To facilitate the manure and other waste materials gravitating down the ramp and also to dilute same to a consistency ideal for digestion, water is sprayed onto the top of the ramp through a series of spray nozzles 52 or the like located just beneath the floor. The lid is fabricated from some smooth-surfaced metal that will not rust such as, for example, galvanized plate. In the particular form shown, the free edge 36 of the lid is bent down at a steeper angle as it enters the pit.

The size of these pits is such that the digesting mass can stay in well over a month while it moves from the inlet to the outlet. This is ample time to insure almost 100% digestion. One ends up with just about half the solids to get rid of that entered the system. Moreover, this digested sludge has nutrient values in it that make it worth recycling. Also, it is far less objectionable from an odor standpoint than the untreated mass. The highly dilute nature of the material in the pit (roughly 95% water) allows it to move easily toward the outlet as fresh material enters the system thus eliminating pumping costs. The free flow of material is, of course, greatly enhanced by the fact that it remains warm and fluid even under very cold ambient conditions. Most important of all to the farmer is the fact that his cattle are not stressed by having to breathe the noxious gases given off by the excrement in the pit, the latter being essentially roofed-over except for the small gap left where the material enters it.

The improved process for emptying manure and other waste materials from pits contained underneath the slatted floors of an animal pen or shelter is also deemed to be novel and consist of the steps of catching the waste passing through the floor in the inclined surface of a ramp-like lid partially covering the pit, flushing the material thus deposited down the ramp by diluting same with water introduced at the top thereof, sealing the pit to prevent exposing the contents thereof to atmosphere except where the waste materials enter, heating the waste materials thus confined to a temperature selected to facilitate anaerobic digestion, seeding the waste materials with bacteria adapted to break down the bio-degradable portion of the waste materials at the selected temperature under anaerobic conditions to produce a bio-gas, recycling and burning a portion of the gas thus generated to heat the digesting mass, and using the incoming fresh waste materials entering the system to push the digested mass out.

What is claimed is:

1. The animal waste treatment system which comprises: wall-enclosed means defining a receptacle adapted to receive and retain animal waste products deposited therein from above; a grid-like floor covering said receptacle for supporting the animals standing thereon while permitting their waste products to pass therethrough; a ramp-like lid covering a substantial portion of the receptacle underneath the floor, said ramp having a downwardly-sloping surface terminating in an edge spaced from the adjacent receptacle wall to leave a gap through which the waste products deposited upon said surface can enter said receptacle, and said lid with said edge thereof immersed in the waste products contained in the receptacle cooperating therewith and with said receptacle walls to seal off that portion of said waste materials located beneath said ramp from the atmosphere; means positioned adjacent the top of the ramp for wetting the waste materials deposited upon its sloping surface and flushing them down into the gap; means within the receptacle for heating the waste materials contained therein to a temperature effective to produce a bio-gas from any bio-degradable constituents contained therein under anaerobic condition conditions when seeded with suitable bacteria; means for drawing the gas from the receptacle underneath the ramp; and, means for withdrawing the solids from the pit following anaerobic digestion thereof, said means being located at a point in the receptacle remote from the gap where the waste materials enter same.

2. The animal waste treatment system as set forth in claim 1 wherein the free edge of the ramp adjacent the gap terminates in a downturned flange immersible in the contents of the receptacle.

3. The animal waste treatment system as set forth in claim 1 wherein the means for withdrawing the solids upon the receptacle includes a discharge tube having an intake end located at a level below the edge of the ramp and an elevated outlet end positioned at a level higher than the latter, and, means defining a catch basin housing the discharge tube, said catch basin having a discharge opening therein located at a level below the level of the outlet end of the discharge tube for evacuating the contents thereof without effecting the level of the waste material in the receptacle.

4. The animal waste treatment system as set forth in claim 1 wherein the means for heating the waste materials is gas-fired and connected to the means for drawing the gas from underneath the ramp so as to use same as a source of fuel.

5. The method of treating animal waste materials deposited in a receptacle by animals standing on a grid-like floor covering the latter which comprises the steps of: covering all but a narrow entryway into said tank with a ramp sloping down toward said entryway, maintaining the depth of waste materials within said receptacle relative to the lower end of said ramp at a level effective to seal the portion of said materials located underneath the latter from the atmosphere, flushing the waste materials deposited on the ramp down into the receptacle through said entryway, seeding the waste materials contained within the receptacle with bacteria capable of breaking the bio-degradable constituents thereof down into bio-gas and solid residues under controlled temperature conditions, heating the waste materials within the receptacle to the temperature conducive to promote anaerobic digestion of said bio-degradable constituents, tapping off the bio-gas from underneath the ramp, and removing the solid residues from the receptacle at a point remote from the entryway.

6. The method of treating animal waste materials as set forth in claim 5 which includes the step of utilizing the bio-gas generated in the receptacle as a source of fuel to heat the contents of the latter.

7. The method of treating animal waste materials as set forth in claim 5 which includes the step of using the waste materials entering the receptacle through the entryway to force the solid residues from said receptacle following digestion thereof.

8. The method of treating animal waste materials as set forth in claim 5 which includes the step of withdrawing the solid residues from the receptacle at a point below the surface thereof and discharging same into an overflow basin at a level above the lower edge of the ramp.

* * * * *